United States Patent [19]

Bunting

[11] Patent Number: 4,695,672
[45] Date of Patent: Sep. 22, 1987

[54] PROCESS FOR EXTRACTIVE-STRIPPING OF LEAN HYDROCARBON GAS STREAMS AT HIGH PRESSURE WITH A PREFERENTIAL PHYSICAL SOLVENT

[75] Inventor: Terry N. Bunting, Odessa, Tex.

[73] Assignee: Advanced Extraction Technologies, Inc., Houston, Tex.

[21] Appl. No.: 854,384

[22] Filed: Apr. 21, 1986

[51] Int. Cl.$^4$ .................................................. F25J 1/02
[52] U.S. Cl. ........................................ 585/867; 62/17; 62/18; 62/20; 55/29; 55/31; 55/68
[58] Field of Search ............... 62/17, 18, 20; 585/867; 55/68, 29, 31

[56] References Cited

U.S. PATENT DOCUMENTS

| | | | |
|---|---|---|---|
| 1,948,777 | 2/1934 | Young et al. | 202/40 |
| 2,187,631 | 1/1940 | Schutt | 196/9 |
| 2,527,951 | 10/1950 | Mayland et al. | 260/681.5 |
| 3,657,375 | 4/1972 | Brunner et al. | 260/679 A |
| 4,235,613 | 11/1980 | Castoe et al. | 62/17 |
| 4,421,535 | 12/1983 | Mehra | 62/17 |
| 4,511,381 | 4/1985 | Mehra | 62/17 |
| 4,526,594 | 7/1985 | Mehra | 62/17 |
| 4,578,094 | 3/1986 | Mehra | 62/17 |
| 4,617,038 | 10/1986 | Mehra | 62/17 |

Primary Examiner—Asok Pal
Attorney, Agent, or Firm—Depaoli & O'Brien

[57] ABSTRACT

A continuous process is described for contacting a raw hydrocarbon gas which is lean and/or at a pressure above about 400 psia with a preferential physical solvent within an extractive-stripping (ES) column to produce a residue gas, containing selected amounts of an undesired hydrocarbon component and lighter hydrocarbons, and a rich solvent, containing the remaining desired hydrocarbons, which is sent to a distilling step in which the product is produced as overhead and the lean solvent is produced as bottoms. To avoid undesirably high bottoms temperatures in the ES column, a portion of the product is recycled to and admixed with the inlet raw gas to the extractive-stripping step to enrich the raw gas. This recycled stream may be: (1) a broad-spectrum recycle stream of gas products, after compression and before cooling thereof, (2) a broad-spectrum recycle stream of liquid products, after compression, cooling, and complete condensation thereof, (3) a relatively narrow-spectrum recycle vapor stream of $C_2$–$C_4$ products, after compression, cooling, and partial condensation thereof, or (4) a relatively narrow-spectrum recycle liquid stream of predominantly $C_4+$ product, for example, after compression, cooling, and partial condensation thereof. This enriching step increases the partial pressure of the heavy hydrocarbon components and thereby permits higher recoveries of ethane and/or propane and/or butane while rejecting undesirable hydrocarbons without having to use an undesirably high temperature within the ES column. Without the recycling step, it is quite difficult to achieve high recoveries of desired components and meet product specifications regarding undesired hydrocarbons in the residue gas stream and in the product stream.

18 Claims, 6 Drawing Figures

SIMPLIFIED PROCESS FLOW WITH RECYCLE

Fig. 1
SIMPLIFIED PROCESS FLOW WITH RECYCLE

Fig. 3
50% RECYCLE

Fig. 4

75% RECYCLE

50% RECYCLE

PROCESS FOR EXTRACTIVE-STRIPPING OF LEAN HYDROCARBON GAS STREAMS AT HIGH PRESSURE WITH A PREFERENTIAL PHYSICAL SOLVENT

BACKGROUND OF THE INVENTION

1. Field of the Invention

This invention relates to contacting a hydrocarbon gas stream with a preferential physical solvent. It particularly relates to separating and recovering ethane and higher boiling hydrocarbons from a hydrocarbon gas stream. It more specifically relates to supplying specific market needs for hydrocarbons by selective recovery of $C_2+$, $C_3+$, $C_4+$, or $C_5+$ hydrocarbons from a hydrocarbon gas stream.

2. Review of the Prior Art

Hydrocarbons must often be recovered from such hydrocarbon gas streams as natural gas, alkylates, reformates, catalytic hydroconversion effluents, hydrofining effluents, and the like. Many recovery processes are available, but countercurrently contacting the upwardly flowing gas stream with a downwardly flowing liquid under conditions furnishing high interfacial surface area is often a preferred recovery process, known as absorption when the liquid is a solvent generally or extraction when the liquid is a preferential physical solvent.

Most physical solvents show some preference among hydrocarbons in a mixture thereof. In other words, they have greater solvency, perhaps because of a stronger physical attraction, for one or more hydrocarbons in such a mixture. This preference is measured by the absorption principle, leading to an alpha or relative volatility. Most of the commonly used lean oils, for example, have relative volatilities of methane over ethane of slightly less than 5.

Lean oils have been used in absorption plants for extracting $C_4+$ hydrocarbons, with some recovery of propane, from hydrocarbon gas streams for many years. The lean oils are non-selective for lighter hydrocarbons, such as ethane and propane, so that relatively large amounts of methane are absorbed, thereby making the separation of ethane and propane from methane quite difficult and expensive. Due to the market demand for lighter hydrocarbons, such as ethane and propane, and the lack of selectivity of lean oils for such components, the absorption processes have been replaced by processes consisting of refrigerated oil absorption, simple refrigeration, cascaded refrigeration, Joule-Thompson, or cryogenic expander processes. The related Mehra Process patents and applications are directed toward use of selected physical solvents having strongly preferential characteristics in absorption/flashing and extractive-stripping steps. The Mehra Process thereby overcomes the disadvantages of non-selectivity of common lean oils for lighter hydrocarbons, such as ethane and propane.

Another disadvantage of the older processes for recovering hydrocarbons from hydrocarbon gas streams is that the recovery levels are quite inflexible. In contrast, the Mehra Process overcomes the inflexibility drawback by effectively utilizing the selectivity and volatility characteristics of preferential physical solvents. Typical recoveries for these processes are compared in Table I, including the extractive-stripping embodiment of the Mehra Process.

TABLE I

COMPARISON OF TYPICAL LIQUID RECOVERIES

| EXTRACTION | ETH-ANE (%) | PRO-PANE (%) | BU-TANES (%) | GASO-LINE (%) |
|---|---|---|---|---|
| ABSORPTION | 5 | 25 | 75 | 87 |
| REFRIGERATED ABSORPTION | 15 | 75 | 90 | 95 |
| SIMPLE REFRIGERATION | 25 | 55 | 93 | 97 |
| CASCADED REFRIGERATION | 70 | 85 | 95 | 100 |
| JOULE-THOMPSON EXPANSION | 70 | 90 | 97 | 100 |
| TURBO-EXPANDER | 85 | 97 | 100 | 100 |
| MEHRA PROCESS | 2-90 | 2-99 | 2-100 | 100 |

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80-85%), but recompression of most of the inlet gas is quite expensive.

In all of the above processes, the ethane plus heavier components are recovered in a specific configuration determined by their composition in the raw hydrocarbon gas stream and equilibrium at the key operating conditions of pressure and temperature within the process. Under poor economic conditions when the ethane price as petrochemical feedstock is less than its equivalent fuel price and when the propane price for feedstock usage is attractive, for example, the operator of a hydrocarbon gas liquid extraction plant is limited as to operating choices because he is unable to minimize ethane recovery and maximize propane recovery in response to market conditions.

The extractive-flashing embodiments of the Mehra Process, as disclosed in U.S. Pat. Nos. 4,421,535, 4,511,381 and 4,526,594, utilize preferential physical solvents for processing natural gas streams by extracting, flashing, compressing, cooling, and condensing the desired components for producing natural gas liquid products. The extractive-flashing embodiments of the Mehra Process combine the advantages of the higher-pressure extraction processes by selectively recovering and letting down the pressure of essentially the desired components, thereby reducing the compression of undesirable components, such as methane, while achieving high levels of component recovery in a flexible manner.

Under the heading, "New NGL Extraction Process", this embodiment of the Mehra Process is described on pages 7 and 8 of *Gas Processors Report*, P.O. Box 33002, Tulsa, Ok. 74153. Commonly owned Ser. No. 759,327 is particularly directed toward processing of nitrogen-rich natural gas streams in this manner.

The extractive-stripping embodiment of the Mehra Process is taught in commonly owned Ser. No. 784,566 and Ser. No. 808,463, which are wholly incorporated herein by reference. This process embodiment utilizes an extractive-stripping (ES) step and eliminates the need for flashing of the rich solvent stream to separate the desired components of a raw gas stream. Residue gas, consisting primarily of methane, leaves the top of the Extractor/Stripper (ES) column while the rich solvent containing the desired hydrocarbon components leaves the bottom of the ES column. The $C_2+$ hydrocarbons are then separated as the natural gas liquid product from the top of the hydrocarbon product column, and the separated solvent is recycled to the ES column for reuse. This process can selectively recover $C_2+$, $C_3+$, $C_4+$, or $C_5+$ hydrocarbons at high recovery levels while rejecting lower-molecular weight hydrocarbons into the residue gas stream.

The rich solvent leaving the bottom of the ES column is let down in pressure to a pressure level consistent with the operation of the product column. This pressure level also obviates the need for a downstream compressor or pump. The rich solvent may be economically heated before entering the product column in order to lower the reboiler heat load and improve separation of hydrocarbons from the physical solvent.

The product column is a typical fractionation-type column in which the selectively extracted hydrocarbons are separated from the preferential physical solvent. The desired hydrocarbons are recovered from the top of the product column as an overhead stream while the hot, lean solvent leaves the bottom of the product column. The temperature at the bottom of the product column is selected to ensure the recovery of all desirable hydrocarbons and is no higher than the boiling point of the physical solvent at the operating pressure. In order to minimize loss of the physical solvent with the product, the column overhead is refluxed with a portion of the condensed hydrocarbons.

In order to minimize energy consumption, the hot, lean physical solvent, leaving the bottom of the product column, is effectively utilized for heating the rich solvent feed to the product column and for reboiling the ES column before returning to the top of the extraction section of the ES column as cool, lean preferential physical solvent.

The rich solvent, leaving the bottom of the ES column, contains only the specified amounts of the undesirable lighter components, such as $C_1$ in $C_2+$ products, in order to meet the product specifications (NGL specifications if the hydrocarbon gas is natural gas). Because such a purity requirement has been combined with selectivity in the ES column, wherein the selection capability of operating pressure is unavailable because it is generally determined by the delivery pressure of the residue gas, only temperature flexibility at the bottom of the ES column is available for meeting the required specification of undesirable components because the other flexibility of flow rate of preferential physical solvent to the ES column is effectively utilized in meeting the selective recovery levels of desired hydrocarbon components of the raw gas stream. The reboiler and the stripping section in the bottom portion of the ES column provide additional selectivity, thereby gaining one more degree of freedom which is effectively utilized by appropriately selecting the reboiling temperature in order to produce the desired rich solvent stream.

Suitable preferential physical solvents, as disclosed in Ser. No. 784,566 and Ser. No. 808,463, are rich in $C_8-C_{10}$ aromatic compounds having methyl, ethyl, or propyl aliphatic groups, including mesitylene, n-propyl benzene, n-butyl benzene, o-xylene, m-xylene, p-xylene, and mixtures thereof, rich being defined as more than 15% by weight. Substantially pure mesitylene is preferred. Suitable sources of these $C_8-C_{10}$ aromatic compounds are aromatic streams, such as in petroleum refineries that are rich in mixed xylenes, $C_9$ alkylaromatics, and other $C_8-C_{10}$ aromatics. These compounds boil in the range of 270°–425° F. and are stable at the process temperatures used in separating mixtures into useful fractions and/or components, such as in distillation, extractive stripping, and extractive distillation operations. Moreover, they are also hydrocarbons which can be left in the liquid products in trace amounts, without interfering with use of such products in gasoline, for example, so that purification of the liquid products is not needed.

A principal refinery source of $C_8-C_{10}$ aromatic feed streams may be found in catalytically reformed naphthas in which a $C_9$ heart cut or extract of the reformate is enriched in $C_9$ alkylbenzenes, a typical reformate containing as much as 57% trimethylbenzenes based on the total content of $C_9$ aromatics. The composition of a $C_9$ heart cut is typically about 2.5, 87.5 and 10 mole % of $C_8$, $C_9$ and $C_{10}$ aromatics, respectively. Other sources of $C_8-C_{10}$ aromatic feedstocks are derived from gasoline producing processes such as the conversion of methanol to gasoline, as described in U.S. Pat. Nos. 3,931,349, 3,969,426, 3,899,544, 3,894,104, 3,904,916 and 3,894,102, and the conversion of synthesis gas to gasoline as described in U.S. Pat. Nos. 4,096,163, 4,279,830, 4,304,871 and 3,254,023, all of which are incorporated by reference. A $C_7-C_9$ mixed aromatic feedstock also may be used and can be derived from various sources including petroleum refinery sources, pyrolysis of coal to produce coke, tar sands, etc.

In petroleum processing operations such as transalkylation, isomerization, and disproportionation, for example, the product streams so produced are further treated, by fractionation and the like, to obtain alkylaromatic streams which contain substantial quantities of alkylbenzenes such as toluene, xylenes, and trimethylbenzenes. A typical alkylaromatic fraction which may be obtained contains predominantly $C_7$ to $C_9$ hydrocarbons and is referred to as crude xylenes.

Refinery streams suitable as preferential physical solvents for the present process are $C_9$ alkylaromatics, a $C_7$ to $C_9$ mixture of alkylaromatics, or a $C_8-C_{10}$ mixture of alkylaromatics. The $C_9$ alkylaromatic hydrocarbons are characterized as mainly monocyclic aromatic compounds, such as alkylbenzenes, which have at least one alkyl group which preferably contains no more than 4 carbon atoms. The $C_9$ aromatic hydrocarbons include, for example, 1,2,3-trimethylbenzene (hemimellitene), 1,2,4-trimethylbenzene (pseudocumene), 1,3,5-trimethylbenzene (mesitylene), isopropylbenzene (cumene), 1,2-methylethylbenzene, 1,3-methylethylbenzene, and 1,4-methylethylbenzene.

The $C_9$ alkylaromatics for use in the present process are conveniently available as product streams from various petroleum processing operations, including gasoline producing processes such as the conversion of methanol to gasoline or the conversion of carbon monoxide and hydrogen (syngas) to gasoline. Catalytic reformates, for example, are particularly preferred since they are enriched in aromatics and the $C_9$ fraction can be readily separated from non-aromatics by extraction with aqueous glycols, typically a Udex unit. The typical composition of extracted $C_9$ reformate and the boiling points of the $C_9$ aromatics contained therein are shown below in Table II.

TABLE II

COMPOSITION OF C$_9$ AROMATICS IN EXTRACTED REFORMATE

| Compound | Boiling Point (°F.) | Freezing Point (°F.) | Wt. % (based on total C$_9$ aromatics) |
|---|---|---|---|
| API Gravity | — | | |
| IBP, °F. | — | | |
| EBP, °F. | — | | |
| Isopropylbenzene | 306 | −141 | 0.6 |
| n-Propylbenzene | 319 | −147 | 5.2 |
| m-Ethyltoluene | 322 | −140 | 17.4 |
| p-Ethyltoluene | 324 | −80 | 8.6 |
| 1,3,5-Trimethylbenzene (mesitylene) | 329 | −49 | 7.6 |
| o-Ethyltoluene | 329 | −114 | 9.1 |
| 1,2,4-Trimethylbenzene (pseudocumene) | 337 | −47 | 41.3 |
| 1,2,3-Trimethylbenzene (hemimellitene) | 349 | −14 | 8.2 |
| Indane | 352 | — | 2.0 |
| | | | 100.0% |

While the quality of crudes may affect the quantity and type of C$_9$ aromatics extracted from a naphtha reformate, about 57 wt. % of the total C$_9$ aromatics are trimethylbenzenes in which pseudocumene, mesitylene and heminellitene are typically produced in the following ratios:

Pseudocumene = 1
Mesitylene = 0.18
Hemimellitene = 0.20

The C$_9$ aromatics may be further characterized as having an initial boiling point range of 230°–280° F., an end boiling point range of 350°–425° F., and an API gravity of 35–60.

A useful, although not ideal, source of preferential physical solvent is primarily a mixture of seven to nine carbon atom alkyl aromatics which include C$_7$ and C$_8$ aromatics, such as toluene, ethylbenzene and xylenes, and C$_9$ alkylaromatics identified in Table II above. Such charge stocks may also be derived from catalytic reformates, pyrolysis gasoline, etc., by distillation and solvent extraction to separate aromatic compounds from aliphatics. Other sources of suitable charge stocks include crude xylene streams, which actually contain alkylaromatics having 7 to 9 carbon atoms, and effluents from toluene transalkylation reaction zones which contain benzene, xylene, C$_9$ aromatics, and aromatics heavier than C$_9$. Mixtures of toluene and C$_9$ alkylaromatics may also be employed. The composition of a typical C$_7$–C$_9$ reformate cut is shown below in Table III.

TABLE III

| Products: | Analysis wt. percent |
|---|---|
| Naphthenes | 0.15 |
| Benzene | 2.03 |
| Toluene | 19.69 |
| Ethylbenzene | 0.004 |
| Paraxylene | 12.04 |
| Metaxylene | 27.64 |
| Orthoxylene | 10.40 |
| p-Ethyltoluene | 0.02 |
| m-Ethyltoluene | 0.06 |
| o-Ethyltoluene | 0.01 |
| Mesitylene | 7.18 |
| Pseudocumene | 15.82 |
| Hemimellitene | 1.93 |
| Ethylxylenes | 0.13 |
| Durene | 1.19 |
| Isodurene | 1.43 |
| Prehnitene | 0.28 |

The C$_7$ to C$_9$ aromatic mixture may be further characterized as having an initial boiling point range of 150° F., an end boiling point range of 350° F., and an API gravity of about 40.

If the hydrocarbon gas stream is sour, it is preferred, in the processes of Ser. No. 784,566 and Ser. No. 808,463, that it be sweetened by contact with an acid-absorbing solvent, such as an amine, for example, before the extraction-stripping process of this invention is utilized. However, if an amine pretreating step is not suitable, the sour hydrocarbon gas stream can be treated according to the instant process. The acidic components are then maintained in liquid-phase or vapor-phase solution or contact, respectively, with the heavier hydrocarbon components until the solution or mixture, as a liquid, can be contacted by an acid-absorbing solvent. Because such post-absorption sweetening is done in liquid phase, the capital cost for equipment is relatively low.

However, when processing must be done without an intermediate flashing stage between the extractor-stripper column and the product column or when extraction must be done at pressures of 400 psia or more or when the inlet gas is quite lean in C$_2$+ hydrocarbons, it becomes difficult to make a clean split between methane as the residue gas and C$_2$+ hydrocarbons as product or between methane and ethane as the residue gas and C$_3$+ hydrocarbons as product or between C$_1$+C$_2$+C$_3$ hydrocarbons as the residue gas and C$_4$+ hydrocarbons as product. Such situations become doubly acute when the pressure is high at the same time that the inlet gas stream is quite lean. Increasing the temperature, such as to above 600° F., to achieve such selectivity has its limitations because such high temperatures may cause undesired breakdown of the solvent and because operating temperatures above 600° F. make it necessary to derate the strength of carbon steel and use stainless steels or steels having special design criteria, thereby increasing capital costs. It is true that clean splits can be made under such conditions, as disclosed in Ser. No. 784,566 and in Ser. No. 808,463, but they may require high energy penalties and difficult processing procedures such as a very high solvent recirculation rate and/or a very high absorption temperature, such as 600°–700° F.

A method for efficiently separating consecutively numbered hydrocarbons in a gas stream without recourse to energy-intensive steps and/or difficult processing procedures, while extractively stripping or distilling a hydrocarbon gas stream with a preferential physical solvent without an intermediate flashing step, is accordingly needed. The following references teach related methods without filling this need.

U.S. Pat. No. 2,570,066 is directed to a method for segregating pure hydrocarbons from hydrocarbon mixtures by distractive distillation in the presence of an aromatic hydrocarbon solvent which is preferably a mono-cyclic aromatic hydrocarbon fraction boiling in the range between 365° and 750° F. Mono-cyclic aromatic hydrocarbons having 10 carbon atoms, exemplified by tetramethylbenzenes such as 1,2,4,5-tetramethylbenzene, 1,2,3,5-tetramethylbenzene, and 1,2,3,4-tetramethylbenzene, and further exemplified by 1,2,-dimethyl-3-ethylbenzene, 1,2-dimethyl-4-ethylbenzene, and the like, are preferred. Durene, isodurene, prehnitene, and mixtures thereof are especially beneficial. The ratios of solvent to feedstock may range from about 1:1 to about 20:1, about 5:1 being preferred.

U.S. Pat. No. 2,573,341 relates to a process for recovering olefinic hydrocarbons and particularly high purity ethylene from coke oven gas, refinery off-gas, and pyrolysis gas, having respective ethylene contents of 4.0, 5.0, and 27.0 mol. %, which are the feedstocks to an absorber-stripper column having a reboiler at its bottom and two intercoolers to remove the heat of extraction. Its overhead is fuel gas, and its bottoms are fed to a succession of distillation columns for separating ethane, ethylene, and propane streams.

U.S. Pat. No. 2,804,448 describes a process in which oil refinery gases from a cracking operation are absorbed with ethane as solvent. The rich solvent is stripped with heat to produce a distillate product. The residue gas is dried and extractively distilled to produce a partially stripped, rich solvent which is stripped with heat to produce a methane-rich gas which is recycled to the inlet gas line ahead of the compressor.

U.S Pat. No. 3,770,622 teaches the use of a physical solvent, having combined oxygen and in which $CO_2$ and $H_2S$ are relatively more soluble than methane, for treating wet natural gas mixtures containing $CO_2$, $H_2S$, and hydrocarbons heavier than methane. Such physical solvents include propylene carbonate, N-methyl pyrrolidone, glycerol triacetate, and polyethylene glycol dimethylether. The physical solvents are designated as selective because $CO_2$ and $H_2S$ are relatively more soluble therein than methane by a factor of 5 or higher under operating conditions and because they have utility for absorbing liquid hydrocarbons during $CO_2$ and $H_2S$ removal from wet natural gas mixtures to enable recovery of gasoline values therefrom by countercurrent absorption at a superatmospheric pressure and a base temperature between $-20°$ F. and $100°$ F. within the absorption zone. The acid gas ($CO_2$, $H_2S$) and hydrocarbons lighter than propane are then flashed and/or stripped from the liquid stream within the lower pressure zone to separate $CO_2$, $H_2S$, and light hydrocarbons from the organic liquid which is next passed to a settling zone where the organic liquid and the liquid hydrocarbons are separated by gravity.

SUMMARY OF THE INVENTION

It is accordingly an object of this invention to provide an energy-efficient process for selectively extracting $C_2+$ hydrocarbons from a hydrocarbon gas stream in accordance with daily changing market conditions to provide a residue gas stream, meeting pipeline specifications and having a selected composition, and a gas or liquid product stream having a selected composition, while using a preferential physical solvent, for extractive-stripping or extractive-distillation of a hydrocarbon gas stream at a substantially uniform pressure throughout the process.

It is a further object to provide such a process for selectively rejecting at least one undesired hydrocarbon, which is consecutive in carbon number with another rejected hydrocarbon of lower molecular weight, of the group consisting of ethane, ethane plus propane, or ethane plus propane plus butane, to a selected degree with the stream of residue gas.

In accordance with these objects and the principles of this invention, a process is herein provided for situations wherein the hydrocarbon gas feed stream is lean and/or when the inlet gas stream is at high pressure, such as above about 400 psi.

It has surprisingly been discovered that these difficulties and limitations may readily be obviated by selectively enriching the inlet gas stream, as by recycling a portion of the entire product stream or by recycling a fractionated part thereof, to be mixed with the inlet hydrocarbon gas feed stream to produce an enriched hydrocarbon gas feed stream for the ES column.

More specifically, a raw inlet gas stream is selectively enriched with a recycle gas stream and contacted with a preferential physical solvent in an Extractor-Stripper (ES) column. The enriched gas enters the ES column below the extraction section and flows upwardly where it contacts lean preferential physical solvent which, after entering the top of the extraction section in the upper portion of the column, flows downwardly countercurrently to the gas stream. The contact takes place over mass transfer surfaces, such as packing or distillation trays. The solvent leaving the bottom of the extraction section and entering the top of the stripping section is rich in $C_1$ and heavier hydrocarbons.

In the stripping section of the extraction column, the reboiling temperature is selected in order to produce the rich solvent stream, consisting essentially of only the economically desired hydrocarbons, and in order to reject the economically undesired hydrocarbons which rise within the ES column to meet and mix with the enriched hydrocarbon feed gas stream.

The $C_1+$-rich solvent from the bottom of the extraction section enters the top of the stripping section of the ES column and flows downwardly, where it comes in contact with the upward-flowing stripped hydrocarbons from the reboiler at the bottom of the ES column. The stripped hydrocarbons consist primarily of undesired hydrocarbons, such as $C_1$ if the desired objective is recovery of $C_2+$ hydrocarbons, or $C_1$ and $C_2$ if the desired objective is the recovery of $C_3+$ hydrocarbons, and so forth, depending upon these objectives.

The rejected, undesirable hydrocarbon stream, flowing upwardly through the stripping section of the ES column, does contain some of the desirable hydrocarbons which are recovered preferentially by the mass transfer principles developed for distillation as the rejected stream flows over the packing or trays of the ES column. The stripped hydrocarbons from the rich solvent leave the stripping section of the ES column, join the incoming raw gas stream and flow together upwardly in the extraction section of the ES column, where lean physical solvent preferentially recovers any contained desired hydrocarbons.

The selective recovery of $C_2+$ components is controlled by variations in flow rates of lean preferential physical solvent within the extraction section of the ES column. Both a high solvent flow rate and a high reboiler temperature cause a high internal recycle rate within the ES column. On either side of the desired split under such conditions, relatively large amounts of $C_a+$ (accepted hydrocarbons) and $C_r-$ (rejected hydrocarbons) flow past each other within the column, the $C_a+$ tending to move downwardly as liquid with the solvent and the $C_r-$ tending to flow upwardly as gases.

Adding the recycle stream does not lower the solvent flow rate. In most cases, the recycle stream adds load to the ES columns which will, in fact, require a higher solvent flow rate than otherwise needed.

Using this recycle allows the reboiler temperature of the ES column to stay within the desired operating range of less than 600° F. It should be understood that this temperature limitation of 600° should not be interpreted to mean that 610° is unacceptable or that 590° is always acceptable. The upper limits will be set by the temperatures at which the solvents break down and will vary for different solvents. In general, however, it is best to avoid temperatures above 600° F. in order not to derate the strength of carbon steel used in the ES column. This recycle step thereby allows the process to operate under reasonable or acceptable process conditions.

The inlet gas stream may be enriched with: (1) a broad-spectrum recycle stream of gas products, after compression and before cooling thereof, (2) a broad-spectrum recycle stream of liquid products, after compression, cooling, and complete condensation thereof, (3) a relatively narrow-spectrum recycle vapor stream of $C_2$–$C_4$ products, after compression, cooling, and partial condensation thereof, or (4) a relatively narrow-spectrum recycle liquid stream of predominantly $C_4+$ product, for example, after compression, cooling, and partial condensation thereof.

DESCRIPTION OF THE PREFERRED EMBODIMENTS

Figure 1:
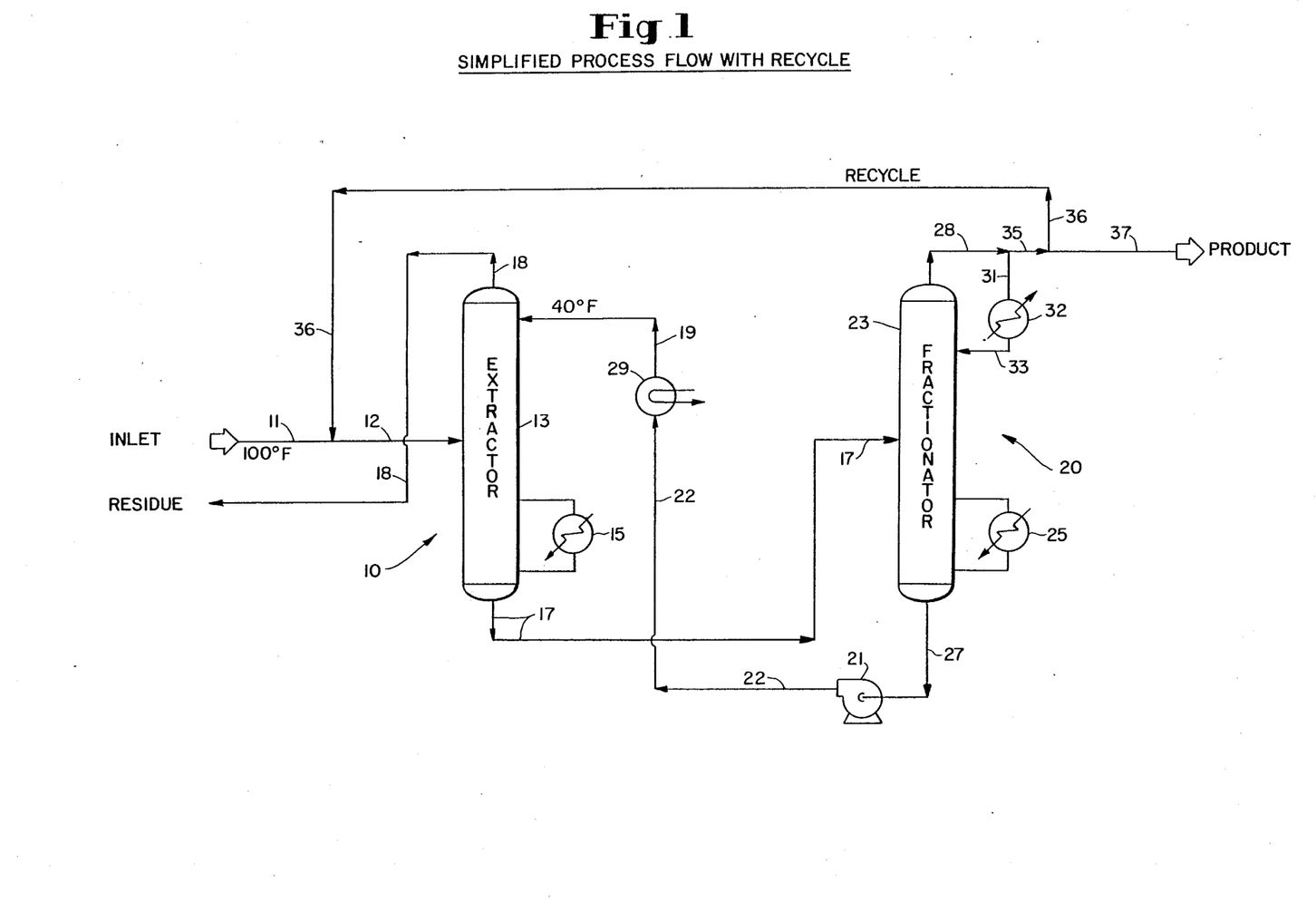
FIG. 1 is a schematic flow sheet for a two-column extractive-stripping process in which a preferential physical solvent selectively extracts and strips $C_2+$ hydrocarbons from an inlet raw hydrocarbon gas stream, with recycle of a portion of the product to the inlet gas stream.

As shown in FIG. 1, the process of this invention for selective extraction of hydrocarbon gas or liquids from a raw hydrocarbon gas stream, which can be dry natural gas, either sour or sweet, comprises combined extraction and stripping (ES) within an ES column to form a rich solvent stream and a residue gas stream, followed by distillation of the rich solvent stream to form the hydrocarbon gas or liquid product stream and a lean solvent stream which is recycled to the extractor-stripper (ES) column. A portion of the product stream is also recycled, either in the hot and compressed gas form or as a liquid after partial or complete condensing thereof, to join the inlet gas stream and form an enriched gas stream which can be extracted and stripped without recourse to undesirably high temperatures.

The inlet gas stream in line 11 is joined by a recycle stream in line 36. The combined stream in line 12 enters extractor (ES) column 13 of extractor unit 10. A residue gas stream leaves as overhead from the top of column 13 through line 18. Bottoms in stripper section of column 13 are heated in reboiler 15. Rich solvent is removed from the bottom of column 13 though line 17. Lean solvent is fed to the top of column 13 through line 19.

The rich solvent stream in line 17 is fed to the approximate midsection of product column 23 which is a part of product column assembly 20. Column 23 is a typical distillation column having a reboiler 25 and a reflux cooler 32. Lean solvent leaves the bottom of column 23 through line 27, is cooled by cooler 29, and is pumped into the top of column 13 through lines 22 and 19 by pump 21.

The overhead from column 23 leaves through line 28, and a portion is bypassed through line 31 and reflux cooler 32 through line 33 into the top of column 23. The remaining portion of the stream in line 28 is split into a recycle portion which enters recycle line 36 and a product portion which leaves the process through line 37. The compressed and vaporous recycle stream in line 36 is recycled to join and enrich the hydrocarbon gas feed stream in line 11 for entering column 13 through line 12. This recycle stream in line 36 may be: (1) a broad-spectrum recycle stream of gas products, after compression and before cooling thereof, (2) a broad-spectrum recycle stream of liquid products, after compression, cooling, and complete condensation thereof, (3) a relatively narrow-spectrum recycle vapor stream of $C_2$–$C_4$ products, after compression, cooling, and partial condensation thereof, or (4) a relatively narrow-spectrum recycle liquid stream of predominantly $C_4+$ product, for example, after compression, cooling, and partial condensation thereof.

Although FIG. 1 shows recycle of the product stream in line 36 to the inlet gas stream in line 11, it should be understood that recycle line 36 can be connected directly to column 13 at the same height as line 11 or at any reasonable distance thereabove and at any position along the circumference of column 13.

EXAMPLES

Using a mainframe computer provided with a simulation software package, computer simulations were run at 100° F. and 450 psia according to FIG. 1 for an inlet hydrocarbon gas feed stream having the following composition:

| Gas Component | Flow rate mols/hr |
| --- | --- |
| Methane | 90.0 |
| Ethane | 5.0 |
| Propane | 2.0 |
| N—Butane | 1.5 |
| N—Pentane | 0.75 |
| N—Hexane | 0.50 |
| N—Heptane | 0.25 |
| TOTAL | 100 |

Conditions in the ES column were as follows in each of the simulations:
Solvent Temperature: 40° F.
Maximum Extractor Bottom Temp.: 600° F.
Minimum Desired Ethane Recovery: 80% or 4 mols/hr.

Maximum Allowable Methane Recovery: 0.2 mols/hr.

EXAMPLE 1

In this first simulation, maximum ethane recovery was sought with no recycle of gaseous product to the inlet gas stream. The results were plotted in FIG. 2.

Figure 2:
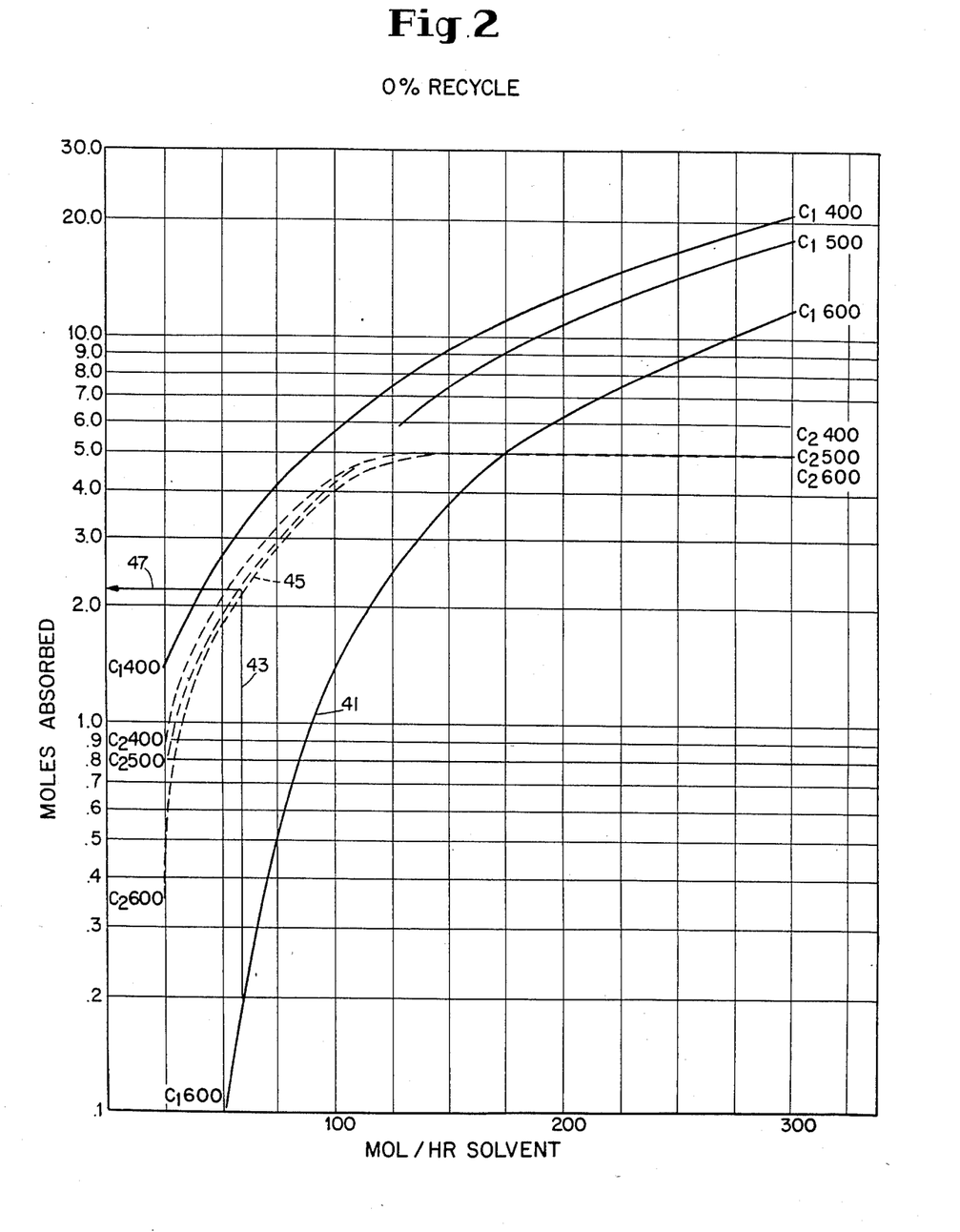
FIG. 2 is a semi-logarithmic plot of mols absorbed for methane and ethane at selected bottoms temperatures versus solvent flow rate in mols/hour, with 0% recycle of gaseous product while seeking maximum ethane recovery and no methane recovery greater than 0.2 mol/hr.

The methane line at 600° F. reaches 0.2 mols of methane absorbed in the rich solvent at a flow rate of 60 mols/hr. of solvent. Drawing a vertical line 43 from the solid methane line 41 to dashed ethane line 45 for ethane recovery at 600° F. and extending that line horizontally as line 47 shows that 2.2 mols of ethane were absorbed in the solvent according to this computer simulation. This recovery equals 44% and therefore does not meet the designed conditions.

EXAMPLE 2

Another computer simulation was conducted for the same solvent and inlet hydrocarbon gas stream at 50% recycle of the product to the inlet gas stream. The results were plotted in FIG. 3.

Figure 3:
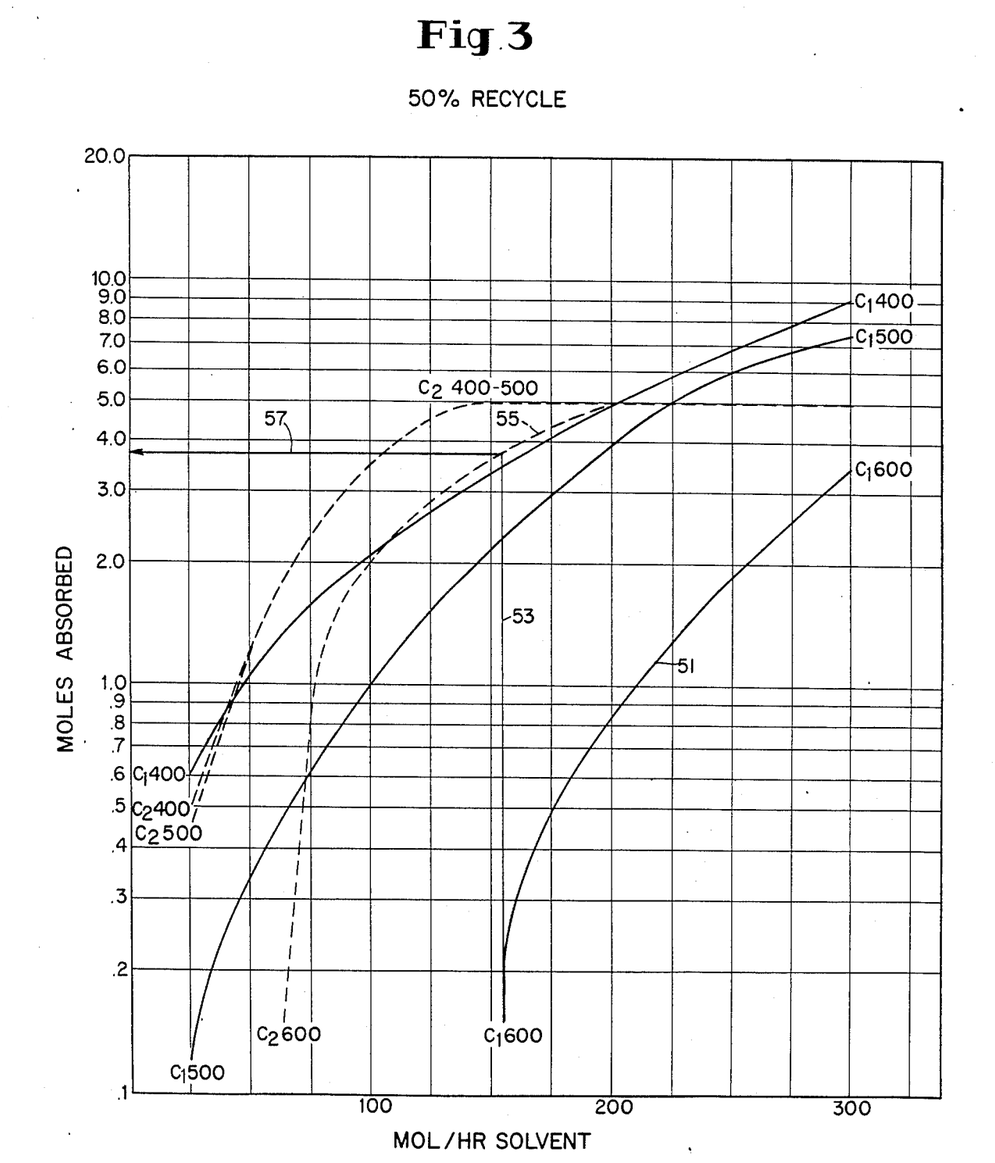
FIG. 3 is a similar plot at 50% recycle for maximum ethane recovery.

The methane line 51 at 600° F. intersects 0.2 mols of methane absorbed at a flow rate of 160 mol/hr of solvent. After drawing a vertical line 53 to the dashed line for ethane recovery at 600° F. and extending a line 57 horizontally to the ordinate, shows ethane recovery to have increased to 3.75 mol/hr or 75%.

This improvement is useful, but the minimum requirements have not yet been met.

EXAMPLE 3

Another computer simulation was made at 75% recycle of the product stream to the inlet gas stream with the same inlet hydrocarbon gas feed stream. The results were plotted in FIG. 4.

Figure 4:
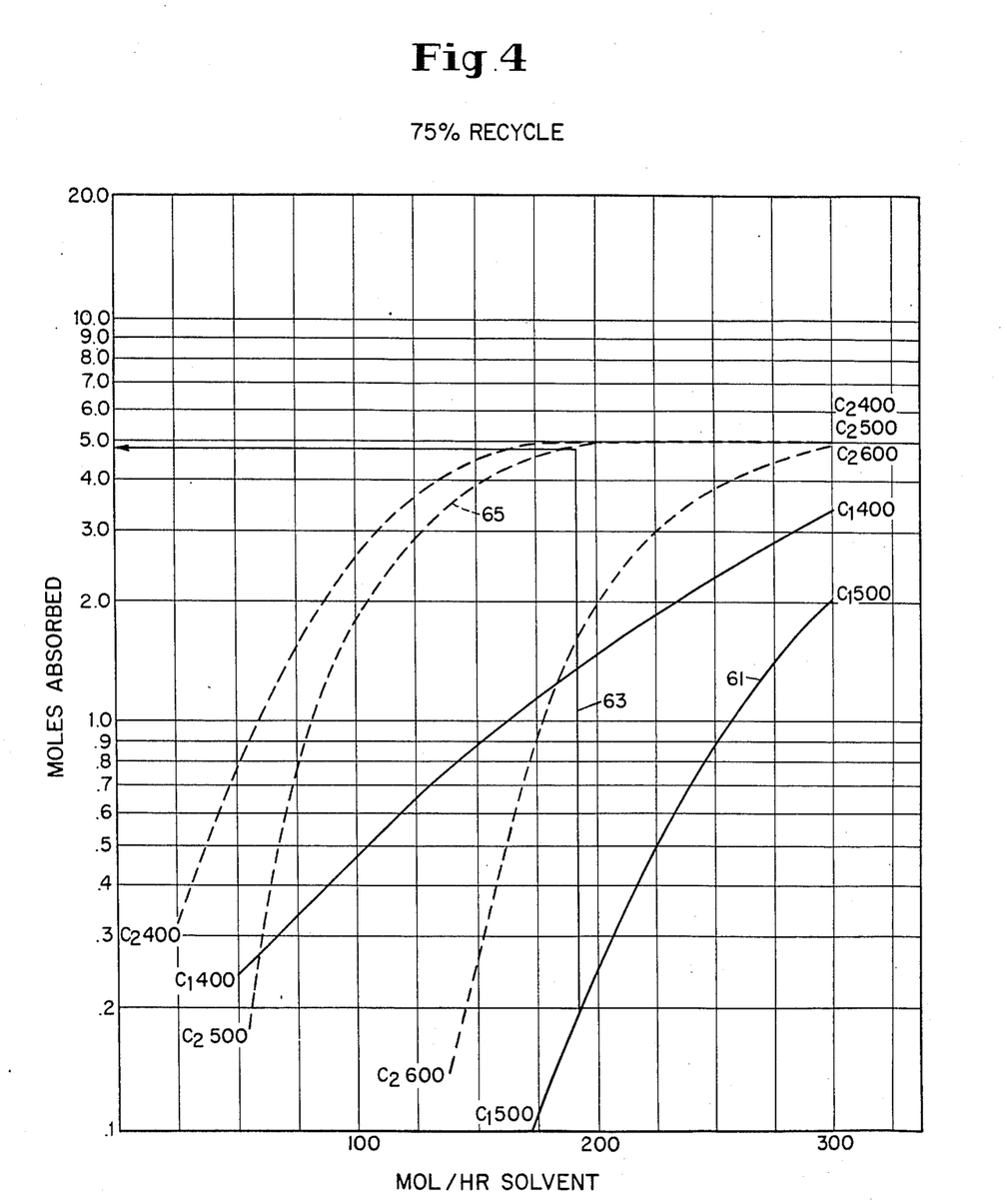
FIG. 4 is another similar plot at 75% recycle for maximum ethane recovery.

The methane line for the run at 600° F. would require an excessively high solvent flow rate. Accordingly, the acceptably high solvent flow rate that is shown in FIG. 4 is for methane at 500° F. This line 61 intersects 0.2 absorbed mols as the maximum limitation for methane recovery at a solvent flow rate of 195 mol/hr of solvent. Drawing line 63 vertically upward to dashed line 65 for ethane recovery at 500° F. and extending a line 67 horizontally to the ordinate indicates 4.8 mols/hr of ethane recovered or 96% at the bottom temperature of only 500° F. This result easily meets the design specifications.

EXAMPLE 4

Another computer simulation was made with the desire to recover a high percentage of propane while minimizing ethane recovery at 0% recycle. The results were plotted in FIG. 5.

Figure 5:
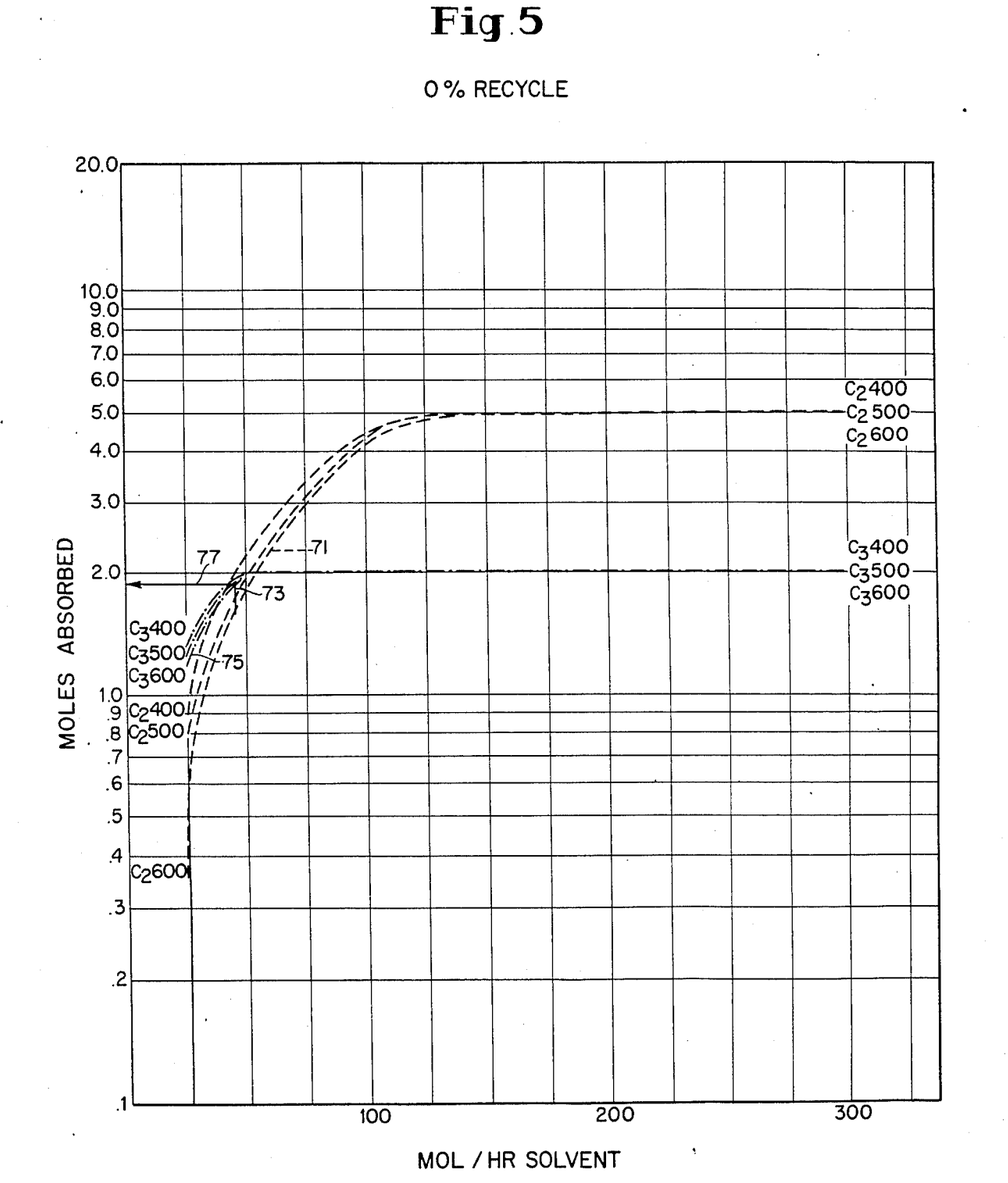
FIG. 5 shows a plot similar to FIGS. 2-4 for high propane recovery while minimizing ethane recovery at 0% recycle.

With design objectives for minimum propane recovery of 95% (1.9 mol/hr) and maximum ethane recovery of 5% (0.2 mol/hr), it can be seen from FIG. 5 that these conditions cannot be met without recycle. Indeed, constructing lines 73, 77 from lines 71,75 in the same manner as done for FIGS. 2–4 shows that a solvent flow rate of 47.5 mols/hr produces 1.9 mols of propane at an ethane recovery of 1.6 mols which is far above the desired maximum recovery for ethane.

EXAMPLE 5

A computer simulation was run for the same hydrocarbon gas feed stream at a recycle of 50% of the product to the inlet gas feed stream. The data were plotted in FIG. 6.

Figure 6:
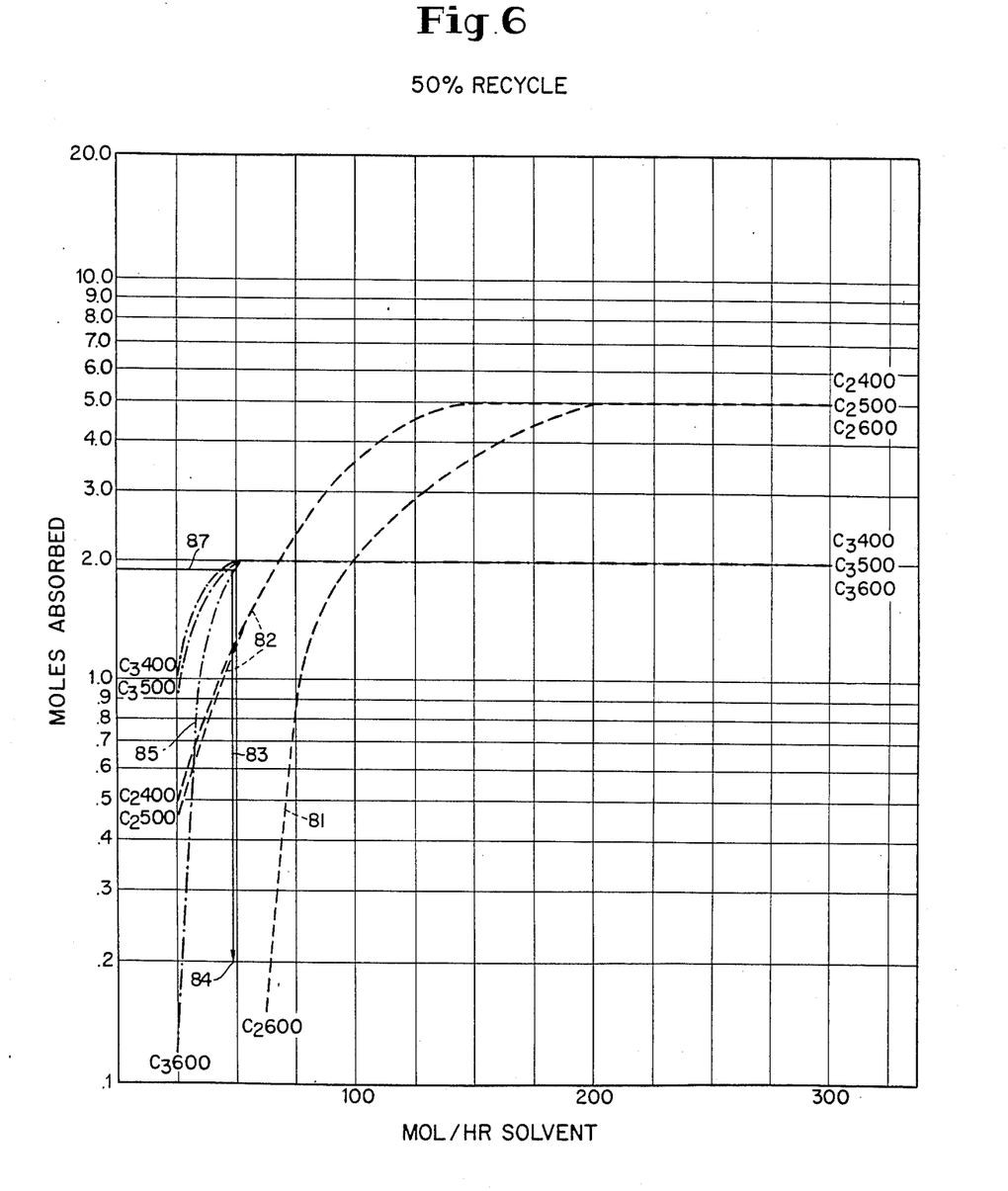
FIG. 6 is a plot similar to FIG. 5 for high propane recovery while minimizing ethane recovery at 50% recycle.

Constructing a horizontal line 87 from 1.9 mols of propane absorbed on the ordinate to propane recovery line 85 at 500° F. and then extending vertical line 83 downward to 0.2 mols of ethane absorbed shows that the desired recoveries can easily be achieved by recycling 50% of the product at a solvent flow rate of 48 mol/hr and at a bottoms temperature of only about 560° F., by extrapolating between lines 81, 82 and through point 84.

A slipstream is taken from the product line and is recycled to the inlet hydrocarbon gas feed stream according to this invention. This enriching step increases the partial pressure of the heavy hydrocarbon components and thereby permits higher recoveries of ethane and/or propane and/or butane while rejecting undesirable hydrocarbons without having to use an undesirable high temperature within the ES column. Without the recycling step, it is quite difficult to achieve high recoveries of desired components and meet product specifications regarding undesired hydrocarbons in the residue gas stream and in the product stream. Additionally, the preferential physical solvent is selected from the group consisting of dialkyl ethers of polyalkylene glycol, N-methyl pyrrollidone, dimethylformamide, propylene carbonate, sulfolane, glycol triacetate, and $C_8$ to $C_{10}$ aromatic compounds having methyl, ethyl, or propyl aliphatic groups sepcifically constituting a sub-group of mesitylene, n-propyl benzene, n-butyl benzene, o-xylene, m-xylene, p-xylene, and mixtures thereof and aromatic streams rich in mixed xylenes and other $C_8$–$C_{10}$ aromatics.

Because it will be readily apparent to those skilled in the art of treating hydrocarbon gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a process for selectively extracting hydrocarbons from a hydrocarbon gas feed stream with a preferential physical solvent which provides selective capability for extremely high recoveries according to any selected degree of a selected hydrocarbon component and heavier hydrocarbons within the group consisting of ethane, propane, butane, and pentane without the need simultaneously to recover hydrocarbons lighter than said selected hydrocarbon component from said hydrocarbon gas feed stream, said recoveries being: (a) ethane in amounts within the range of 2–100%, (b) propane in amounts within the range of 2–100%, (c) butane in amounts within the range of 2–100%, or (d) pentanes and higher molecular weight hydrocarbons in amounts ranging up to 100% by the following steps:

(a) selectively extracting and stripping said hydrocarbon gas feed stream with said physical solvent to produce a residue hydrocarbon gas stream of pipeline specifications and a rich solvent stream containing ethane and heavier hydrocarbon components, whereby said rich solvent stream consists essentially of only economically desired hydrocarbons, said preferential physical solvent being selective for said ethane and heavier hydrocarbon components of the gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor determined by the multiplication of relative volatility of methane over ethane by the solubility of ethane in solvent, in standard cubic feet of ethane per gallon of solvent, is at least 1.25; and (b) distilling said rich solvent to produce: (1) said selected hydrocarbon component and heavier hydrocarbons as overhead product, the amount of each recovered hydrocarbon component that is lower in molecular weight than said selected hydrocarbon component being less than the recovered amount of said selected hydrocarbon component, and (2) said physical solvent as bottoms for feeding to said extracting and stripping step, wherein the need exists to avoid an excessive solvent flow rate and high reboiler temperatures when said hydrocarbon gas stream is lean and/or when said hydrocarbon gas feed stream is at a pressure above about 400 psia, the improvement comprising the selective enrichment of said hydrocarbon gas feed stream with recycle of a selected portion of said overhead product to said extracting and stripping step, whereby said extremely high recoveries according to said any selected degree are feasible without said excessive solvent flow rates or said high reboiler temperatures.

2. The improved process of claim 1, wherein said high reboiler temperatures to be avoided are generally above 600° F.

3. The improved process of claim 1, wherein said solvent flow rates are within the range of 0.001 to 0.5 gallon of said solvent per SCF of said hydrocarbon gas stream fed to said extracting and stripping Step (a).

4. The process of claim 3, wherein said solvent is selected from the group consisting of mesitylene, n-propyl benzene, n-butyl benzene, o-xylene, m-xylene, p-xylene, and mixtures thereof, and aromatic streams rich in mixed xylenes and other $C_8$–$C_{10}$ aromatics.

5. The process of claim 4, wherein said aromatic streams comprise a $C_9$ heart cut or extract of catalytically reformed naphtha which is enriched in $C_9$ alkylbenzenes.

6. The process of claim 5, wherein said $C_9$ aromatics extracted from a naphtha reformate are characterized as having an initial boiling point range of 230°–280° F., an end boiling point range of 350°–425° F., and an API gravity of 35–60.

7. The process of claim 4, wherein said $C_8$–$C_{10}$ aromatic streams are $C_9$ alkylaromatics derived from gasoline producing processes.

8. The process of claim 7, wherein said $C_8$–$C_{10}$ aromatic streams are $C_9$ alkylaromatics derived from conversion of methanol to gasoline.

9. The process of claim 7, wherein said $C_8$–$C_{10}$ aromatic streams are $C_9$ alkylaromatics derived from conversion of syngas to gasoline.

10. The process of claim 4, wherein said $C_8$–$C_{10}$ aromatic streams are $C_9$ alkylaromatics derived from pyrolysis of coal to produce coke.

11. The process of claim 4, wherein said $C_8$–$C_{10}$ aromatic streams are alkylaromatic streams which contain substantial quantities of alkylbenzenes and are produced by petroleum processing operations selected from the group consisting of transalkylation, isomerization, and disproportionation.

12. The process of claim 11, wherein said alkylaromatic streams are mixed xylenes.

13. The process of claim 4, wherein said contacting of said Step (a) is at pipeline pressures and wherein said any selected degree of recoveries of said selected hydrocarbon and heavier hydrocarbons is selectively adjustable in response to market conditions.

14. The process of claim 1, wherein said recycle is a fractionated part of said overhead product.

15. The process of claim 1, wherein said recycle is a broad-spectrum recycle stream of gas products, after compression and before cooling thereof.

16. The process of claim 1, wherein said recycle is a broad-spectrum recycle stream of liquid products, after compression, cooling, and complete condensation thereof.

17. The process of claim 1, wherein said recycle is a relatively narrow-spectrum recycle vapor stream of $C_2$–$C_4$ products, after compression, cooling, and partial condensation thereof.

18. The process of claim 1, wherein said recycle is a relatively narrow-spectrum recycle liquid stream of predominantly $C_4+$ product, after compression, cooling, and partial condensation thereof.

* * * * *